US009215366B2

(12) United States Patent
Morita

(10) Patent No.: US 9,215,366 B2
(45) Date of Patent: Dec. 15, 2015

(54) ENDOSCOPE SYSTEM, CONTROL METHOD, AND IMAGING DEVICE

(71) Applicant: OLYMPUS CORPORATION, Tokyo (JP)

(72) Inventor: Yasunori Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 13/750,343

(22) Filed: Jan. 25, 2013

(65) Prior Publication Data

US 2013/0137929 A1 May 30, 2013

Related U.S. Application Data

(63) Continuation of application No. PCT/JP2011/066034, filed on Jul. 14, 2011.

(30) Foreign Application Priority Data

Aug. 6, 2010 (JP) .................................. 2010-177298

(51) Int. Cl.
*A61B 1/00* (2006.01)
*A61B 1/04* (2006.01)
(Continued)

(52) U.S. Cl.
CPC ........ *H04N 5/23216* (2013.01); *A61B 1/00009* (2013.01); *A61B 1/00188* (2013.01); *A61B 1/04* (2013.01); *G02B 23/2484* (2013.01)

(58) Field of Classification Search
CPC ........... A61B 1/00096; A61B 1/00163; A61B 1/00188; A61B 1/0669; A61B 5/1076
USPC .......... 600/117, 118, 160, 178, 180, 181, 109
See application file for complete search history.

(56) References Cited

U.S. PATENT DOCUMENTS 6,002,137 A 12/1999 Hayashi
8,228,370 B2 7/2012 Namii et al.
(Continued)

FOREIGN PATENT DOCUMENTS

JP 06-261256 9/1994
JP 06-342122 12/1994
(Continued)

OTHER PUBLICATIONS

International Search Report dated Oct. 18, 2011 issued in PCT/JP2011/066034.

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An endoscope system includes an imaging section that captures an object via an optical system and an image sensor, an observation state determination section that determines the observation state of the object captured by the imaging section, and an aperture control section that controls the state of an aperture included in the optical system based on the observation state, the aperture control section controlling the state of the aperture so that the resolution determined by the diffraction limit due to the aperture is equal to or higher than a resolution determined by the image sensor when the observation state determination section has determined that the observation state is a first observation state, and stopping down the aperture as compared with the state of the aperture in the first observation state when the observation state determination section has determined that the observation state is a second observation state.

18 Claims, 20 Drawing Sheets

(51) Int. Cl.
*A61B 1/06* (2006.01)
*H04N 5/232* (2006.01)
*G02B 23/24* (2006.01)

(56) References Cited

U.S. PATENT DOCUMENTS

| | | | |
|---|---|---|---|
| 2002/0075388 A1 | 6/2002 | Koyama et al. | |
| 2002/0107444 A1* | 8/2002 | Adler | 600/424 |
| 2004/0155975 A1* | 8/2004 | Hart et al. | 348/335 |
| 2005/0237606 A1* | 10/2005 | Greenberg | 359/388 |
| 2006/0164533 A1* | 7/2006 | Hsieh et al. | 348/317 |
| 2010/0283842 A1* | 11/2010 | Guissin et al. | 348/68 |

FOREIGN PATENT DOCUMENTS

| | | |
|---|---|---|
| JP | 08-181909 | 7/1996 |
| JP | 08-327917 | 12/1996 |
| JP | 10-225427 | 8/1998 |
| JP | 2002-131832 | 5/2002 |
| JP | 2003-134393 | 5/2003 |
| JP | 2010-057619 | 3/2010 |
| JP | 2011-147707 | 8/2011 |
| JP | 2011-193983 | 10/2011 |

* cited by examiner

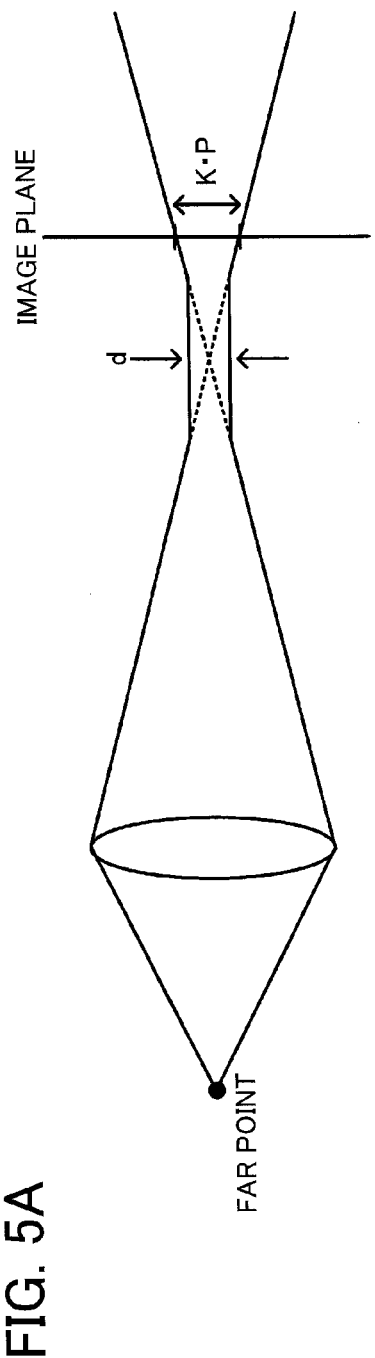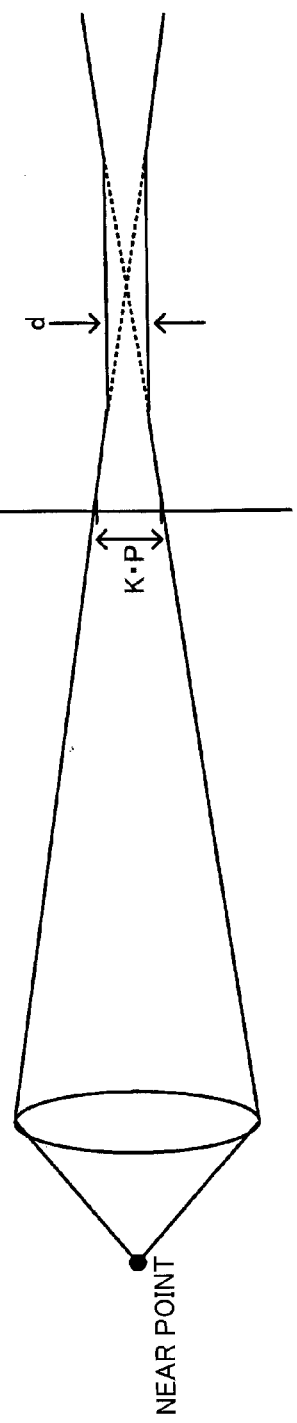
FIG. 5A
FIG. 5B

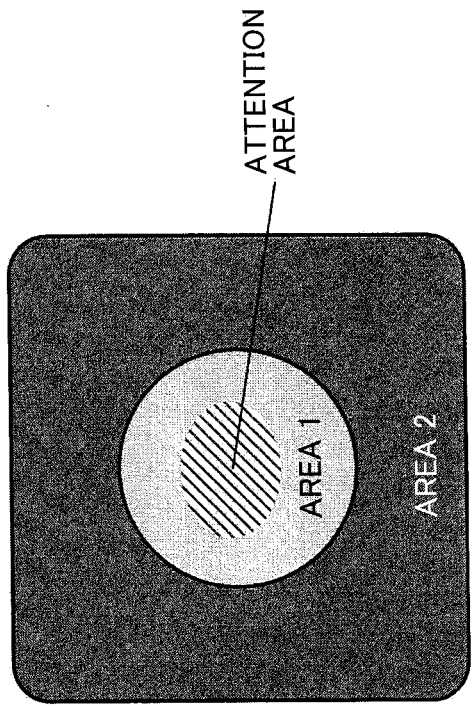
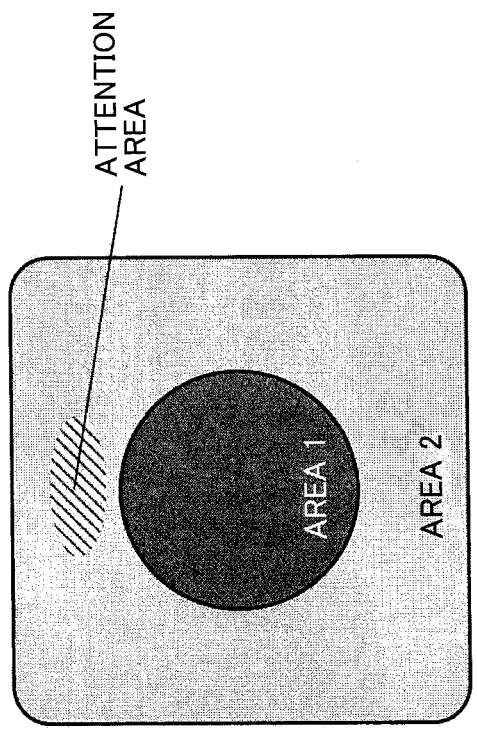

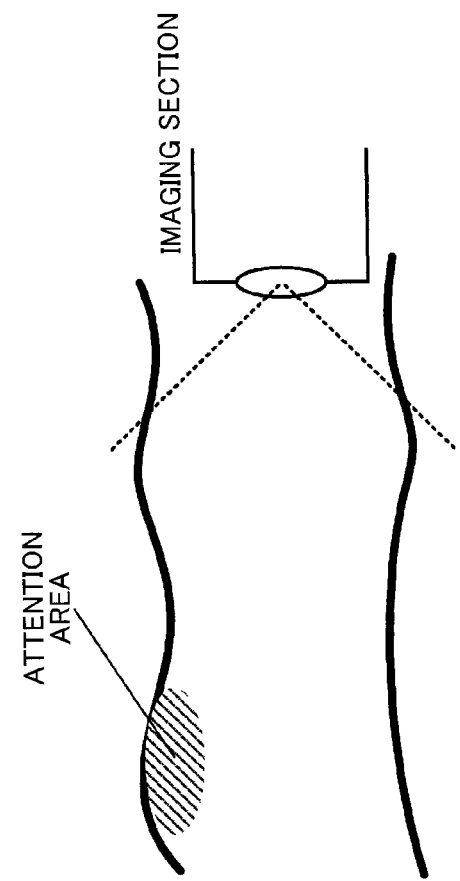
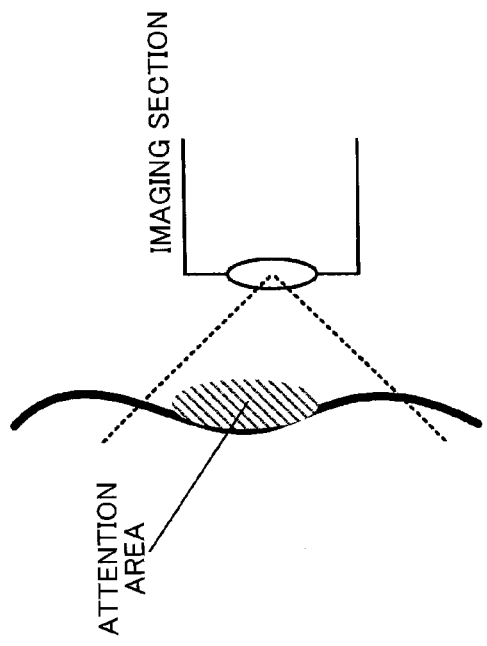
FIG. 22A
FIG. 22B

ENDOSCOPE SYSTEM, CONTROL METHOD, AND IMAGING DEVICE

CROSS REFERENCE TO RELATED APPLICATION

This application is a continuation of International Patent Application No. PCT/JP2011/066034, having an international filing date of Jul. 14, 2011, which designated the United States, the entirety of which is incorporated herein by reference. Japanese Patent Application No. 2010-177298 filed on Aug. 6, 2010 is also incorporated herein by reference in its entirety.

BACKGROUND

The present invention relates to an endoscope system, a control method, an imaging device, and the like.

An imaging device such as an endoscope may be required to generate a deep-focus image inside a body cavity in order to facilitate a doctor's diagnosis. However, the object captured using an endoscope does not necessarily have a planar shape, but may have a tubular shape (e.g., large intestine or bronchial tube). Therefore, a deep-focus image has been implemented by increasing the depth of field of an endoscope by utilizing an optical system having a relatively large aperture value (hereinafter may be referred to as "F-number").

In recent years, a megapixel image sensor has been used for an endoscope system. However, the size of the image sensor provided on the end of the endoscope system is limited, and it is necessary to reduce the pixel pitch (vertical and horizontal dimensions of one pixel) in order to increase the number of pixels. The depth of field of an optical system is determined by the size of the permissible circle of confusion. Since an image sensor having a large number of pixels has a small pixel pitch and a small permissible circle of confusion, the depth of field of the imaging device decreases. In this case, the depth of field may be maintained by increasing the aperture value of the optical system. According to this method, however, the optical system darkens, and noise increases, so that the image quality deteriorates. Moreover, the effects of diffraction increase as the aperture value increases, so that the imaging performance deteriorates. Accordingly, a high-resolution image cannot be obtained even if the number of pixels of the image sensor is increased.

JP-A-6-342122 discloses a technique that increases the depth of field and the intensity of light of an endoscope system that includes a variable aperture and has the above problem. According to the technique disclosed in JP-A-6-342122, the range of the depth of field can be observed by appropriately synchronizing the focus function and the aperture operation.

JP-A-8-181909 discloses a technique that suppresses a change in resolution based on the aperture value. In JP-A-8-181909, a constant resolution is obtained independently of the aperture value by decreasing the degree of contour enhancement when decreasing the aperture value of the optical system, and increasing the degree of contour enhancement when increasing the aperture value of the optical system.

SUMMARY

According to one aspect of the invention, there is provided an endoscope system comprising:

an imaging section that captures an object via an optical system and an image sensor;

an observation state determination section that determines an observation state of the object captured by the imaging section; and an aperture control section that controls a state of an aperture included in the optical system based on the observation state determined by the observation state determination section, the aperture control section controlling the state of the aperture so that a resolution determined by a diffraction limit due to the aperture of the optical system is equal to or higher than a resolution determined by the image sensor when the observation state determination section has determined that the observation state is a first observation state, and stopping down the aperture as compared with the state of the aperture in the first observation state when the observation state determination section has determined that the observation state is a second observation state.

According to another aspect of the invention, there is provided a control method comprising:

capturing an object via an optical system and an image sensor;

determining an observation state of the object that has been captured;

controlling a state of an aperture included in the optical system so that a resolution determined by a diffraction limit due to the aperture of the optical system is equal to or higher than a resolution determined by the image sensor when it has been determined that the observation state is a first observation state; and stopping down the aperture as compared with the state of the aperture in the first observation state when it has been determined that the observation state is a second observation state.

According to another aspect of the invention, there is provided an imaging device comprising:

an imaging section that captures an object via an optical system and an image sensor;

an observation state determination section that determines an observation state of the object captured by the imaging section; and an aperture control section that controls a state of an aperture included in the optical system based on the observation state determined by the observation state determination section, the aperture control section controlling the state of the aperture so that a resolution determined by a diffraction limit due to the aperture of the optical system is equal to or higher than a resolution determined by the image sensor when the observation state determination section has determined that the observation state is a first observation state, and stopping down the aperture as compared with the state of the aperture in the first observation state when the observation state determination section has determined that the observation state is a second observation state.

BRIEF DESCRIPTION OF THE DRAWINGS

FIG. 5A illustrates the far point of the depth of field, and FIG. 5B illustrates the near point of the depth of field.

FIG. 21A illustrates a case where a peripheral area is brighter than a center area, and FIG. 21B illustrates a case where a center area is brighter than a peripheral area.

FIG. 22A illustrates a case where a hollow tubular object is captured, and FIG. 22B illustrates a case where an imaging section faces an object.

DESCRIPTION OF EXEMPLARY EMBODIMENTS

Figure 1A:
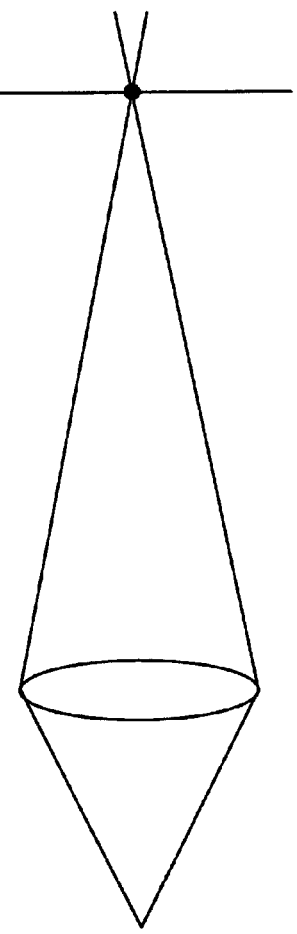
FIG. 1A illustrates an example of convergence of light when the diffraction limit is not taken into account.

According to one embodiment of the invention, there is provided an endoscope system comprising:

an imaging section that captures an object via an optical system and an image sensor;

an observation state determination section that determines an observation state of the object captured by the imaging section; and an aperture control section that controls a state of an aperture included in the optical system based on the observation state determined by the observation state determination section, the aperture control section controlling the state of the aperture so that a resolution determined by a diffraction limit due to the aperture of the optical system is equal to or higher than a resolution determined by the image sensor when the observation state determination section has determined that the observation state is a first observation state, and stopping down the aperture as compared with the state of the aperture in the first observation state when the observation state determination section has determined that the observation state is a second observation state.

According to another embodiment of the invention, there is provided a control method comprising:

capturing an object via an optical system and an image sensor;

determining an observation state of the object that has been captured;

controlling a state of an aperture included in the optical system so that a resolution determined by a diffraction limit due to the aperture of the optical system is equal to or higher than a resolution determined by the image sensor when it has been determined that the observation state is a first observation state; and stopping down the aperture as compared with the state of the aperture in the first observation state when it has been determined that the observation state is a second observation state.

According to another embodiment of the invention, there is provided an imaging device comprising:

an imaging section that captures an object via an optical system and an image sensor;

an observation state determination section that determines an observation state of the object captured by the imaging section; and an aperture control section that controls a state of an aperture included in the optical system based on the observation state determined by the observation state determination section, the aperture control section controlling the state of the aperture so that a resolution determined by a diffraction limit due to the aperture of the optical system is equal to or higher than a resolution determined by the image sensor when the observation state determination section has determined that the observation state is a first observation state, and stopping down the aperture as compared with the state of the aperture in the first observation state when the observation state determination section has determined that the observation state is a second observation state.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

Figure 1B:
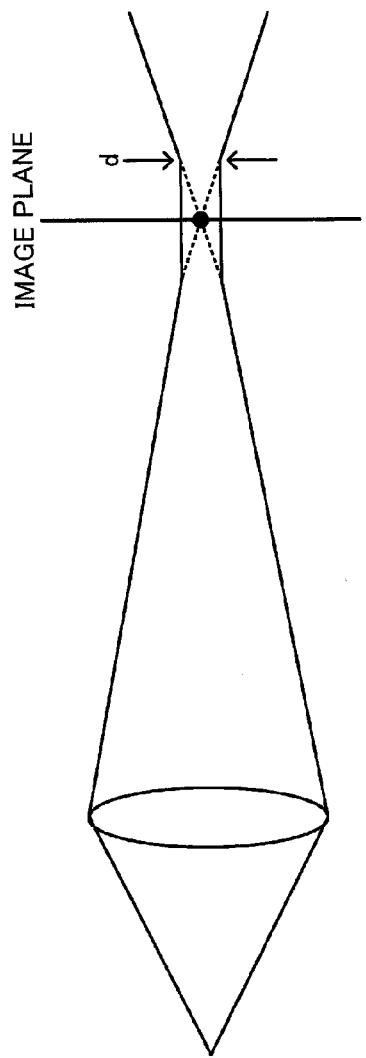
FIG. 1B illustrates an example of convergence of light when the diffraction limit is taken into account.
Figure 2:
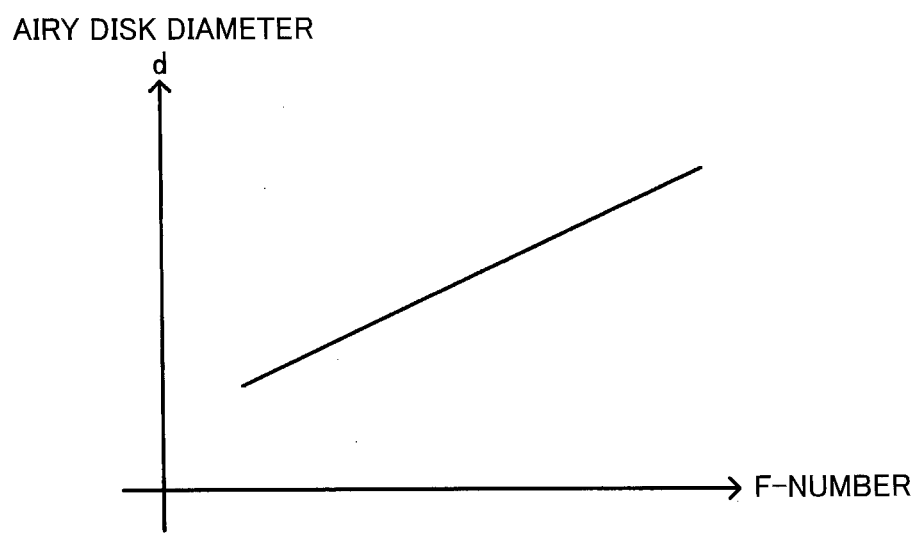
FIG. 2 illustrates the relationship between the Airy disk diameter d and the F-number F.

The meanings of the terms "diffraction limit" and "Airy disk" are described below. Since light has wave properties, a diffraction phenomenon occurs. Therefore, light is not converged (focused) at an infinitely small point (see FIG. 1A), but has a certain size at the convergence point (see FIG. 1B). This limit is referred to as "diffraction limit", and a spot formed by converged light is referred to as "Airy disk". In FIG. 1B, d indicates the Airy disk diameter. The Airy disk diameter d increases as a result of increasing the F-number (i.e., stopping down the aperture). The Airy disk diameter d and the F-number have a relationship illustrated in FIG. 2.

Figure 3:
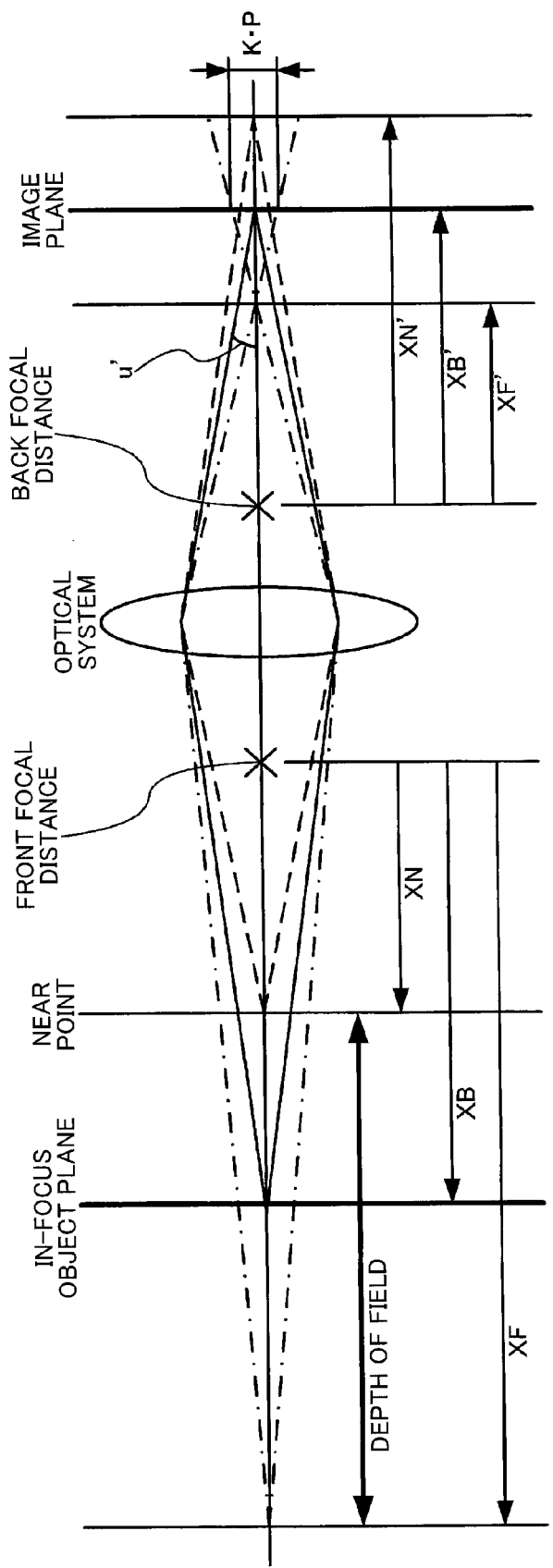
FIG. 3 illustrates the depth of field.

The depth of field is described in detail below with reference to FIG. 3. In FIG. 3, a right arrow indicates a vector having a positive value, and a left arrow indicates a vector having a negative value. When an image sensor having a pixel pitch (vertical and horizontal dimensions of one pixel) of P is disposed at a distance XB' from the back focal distance of the optical system, the position (in-focus object plane) of the object at which the optical system has the best imaging performance in the image plane of the image sensor is the position at a distance XB from the front focal distance of the optical system. The distance XB is uniquely calculated by the following Newton's equation using the distance XB'. Note that f is the focal length of the optical system.

$$XB \cdot XB' = -f^2 \quad (1)$$

When the object is moved to the position at a distance XN from the front focal distance of the optical system, the image plane position XN' moves from the image plane in the direction opposite to the optical system. However, when the diameter of the circle of confusion in the image plane is smaller than the resolution K·P (where, K is a coefficient determined by a filter array and an interpolation process) of the imaging device, the object positioned at the distance XN from the front focal distance of the optical system is considered to be in focus. In this case, the resolution K·P is determined to be the diameter of the permissible circle of confusion.

A range in which the diameter of the circle of confusion in the image plane is equal to or smaller than the resolution K·P is defined as the near point-side depth of field, and the position of the object at which the diameter of the circle of confusion coincides with the resolution K·P is hereinafter referred to as "near point". The position of the near point is hereinafter expressed by the position at the distance XN from the front focal distance. The above definition is similarly applied to the far point-side depth of field. The far point-side position of the object at which the diameter of the circle of confusion coincides with the resolution K·P is hereinafter referred to as "far point". The position of the far point is hereinafter expressed by the position at the distance XF from the front focal distance.

The diameter of the circle of confusion in the image plane when the object is positioned at the near point is approximated by $2(XN'-XB') \cdot NA'$ using the numerical aperture NA ($=\sin(u')$) (where, u' is the angle formed by the optical axis and a beam that enters the image plane illustrated in FIG. 3) of the optical system. Since the diameter of the circle of confusion coincides with the resolution K·P when the object is positioned at the near point, the following expression (2) is obtained.

$$2(XN'-XB') \cdot NA' = K \cdot P \quad (2)$$

Transforming the expression (2) using the following expression (3) (i.e., a relational expression of the F-number and the numerical aperture) yields the following expression (4). Note that F is the F-number of the optical system.

$$F = \frac{1}{2NA'} \quad (3)$$

$$XN' - XB' = K \cdot P \cdot F \quad (4)$$

Transforming the expression (4) using the Newton's equation (1) yields the following expression (5) (i.e., a relational expression of the near point-side depth of field).

$$\frac{1}{XB} - \frac{1}{XN} = \frac{K \cdot P \cdot F}{f^2} \quad (5)$$

A relational expression of the far point-side depth of field calculated in the same manner as the near point-side depth of field is shown by the following expression (6).

$$\frac{1}{XF} - \frac{1}{XB} = \frac{K \cdot P \cdot F}{f^2} \quad (6)$$

The expressions (5) and (6) can be transformed into the following expressions. The near point (i.e., the position at the distance XN from the front focal distance) and the far point (i.e., the position at the distance XF from the front focal distance) can be calculated using the following expressions.

$$XN = \frac{f^2 \cdot XB}{f^2 - XPF \cdot XB} \quad (7)$$

$$XF = \frac{f^2 \cdot XB}{f^2 + XPF \cdot XB} \quad (8)$$

Specifically, when the focal length f, the F-number F, the coefficient K, and the in-focus object plane XB of the optical system are constant, the near point and the far point approach the in-focus object plane (i.e., the depth of field decreases) as the resolution K·P of the imaging device decreases.

The depth of field can be increased by increasing the F-number F or the coefficient K of the resolution K·P of the imaging device. The following description illustrates an example in which the coefficient K is constant, and the depth of field is changed by changing the F-number F.

Figure 4:
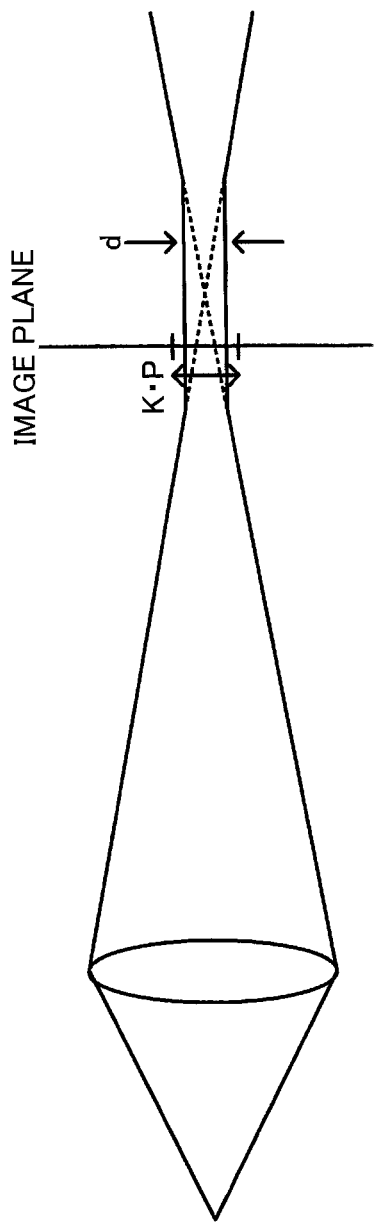
FIG. 4 illustrates an example when the Airy disk diameter d is smaller than the size (K·P) of the permissible circle of confusion.

The relationship between the permissible circle of confusion and the Airy disk is described below. When the Airy disk diameter d is smaller than the size (K·P) of the permissible circle of confusion (see FIG. 4), the depth of field is determined by the above concept (see FIGS. 5A and 5B).

Figure 6:
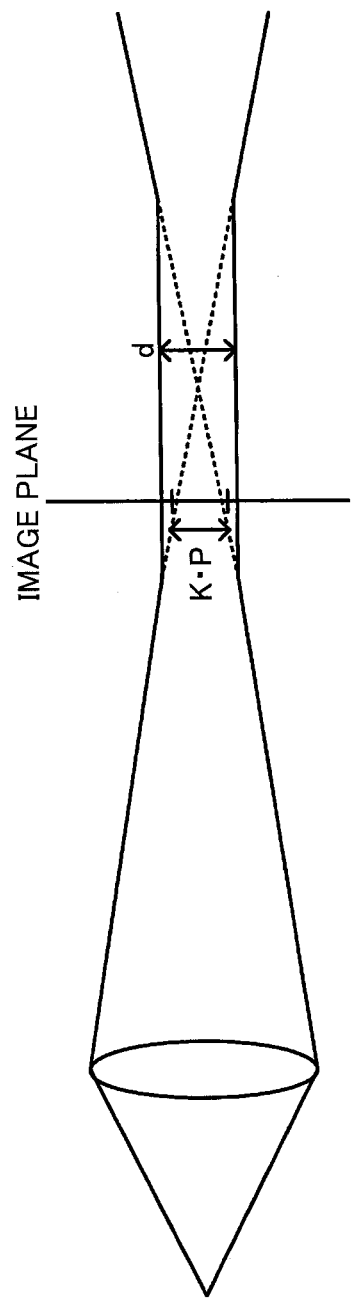
FIG. 6 illustrates an example when the Airy disk diameter d is larger than the size (K·P) of the permissible circle of confusion.

When the Airy disk diameter d is larger than the size (K·P) of the permissible circle of confusion (see FIG. 6), the depth of field is determined by the Airy disk diameter d instead of the size (K·P) of the permissible circle of confusion. As illustrated in FIG. 6, since the size of the circle of confusion is equal to or larger than the Airy disk diameter d, the size of the circle of confusion does not become equal to or smaller than the Airy disk diameter d even when the object is in focus. In this case, the size of the permissible circle of confusion is the Airy disk diameter d.

Figure 7A:
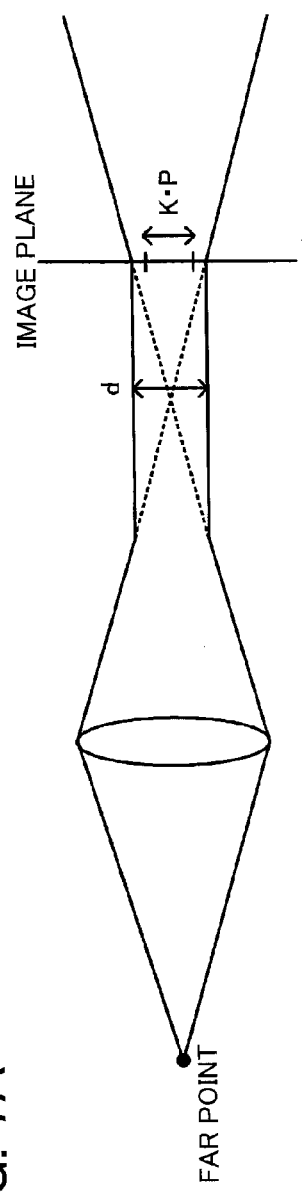
FIG. 7A illustrates the far point of the depth of field.
Figure 7B:
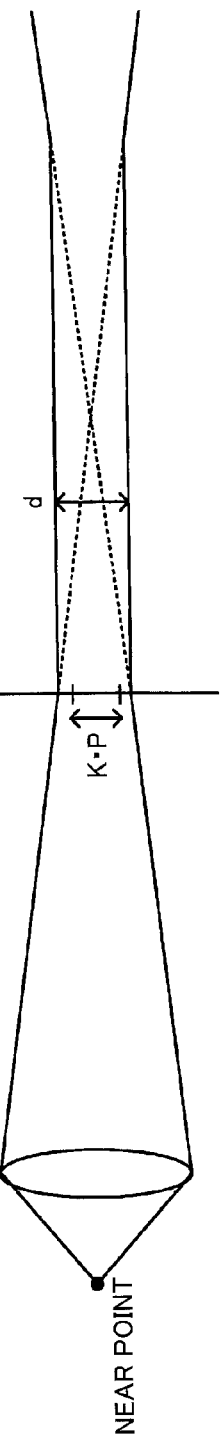
FIG. 7B illustrates the near point of the depth of field.

Therefore, the depth of field can be increased (see FIGS. 7A and 7B) although the resolution decreases due to an increase in the size of the permissible circle of confusion.

Several aspects of the invention propose a method that sets the Airy disk diameter d to be larger than the size (K·P) of the permissible circle of confusion when the doctor searches a lesion while moving the end of the endoscope (search state), and sets the Airy disk diameter d to be smaller than the size (K·P) of the permissible circle of confusion when the doctor examines an attention area without moving the end of the endoscope (examination state) to implement deep focus (i.e., a state in which the depth of field is deep) while acquiring an image having a resolution achieved by fully utilizing the performance of the imaging device.

In the search state, the depth of field is increased in spite of a decrease in resolution by increasing the F-number (stopping down the aperture) (i.e., increasing the effects of the diffraction limit). In the examination state, an image having a high resolution determined by the imaging device is acquired in spite of a shallow depth of field by decreasing the F-number (i.e., suppressing the effects of the diffraction limit)

Figure 8:
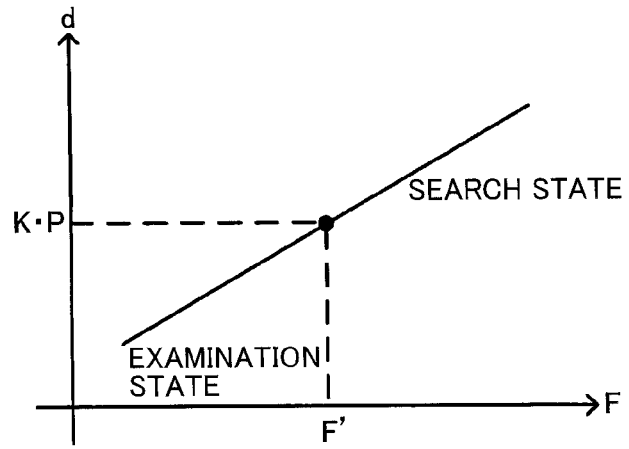
FIG. 8 illustrates the relationship between a first observation mode (examination state) and a second observation mode (search state).

FIG. 8 illustrates the search state and the examination state. For example, the observation state is determined to be the search state or the examination state based on the point where d=K·P.

An advantage obtained by utilizing the search state when implementing deep focus is described below.

Figure 9:
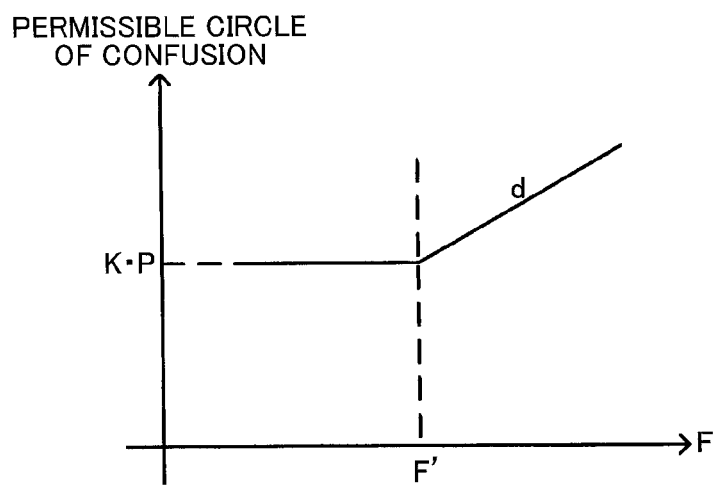
FIG. 9 illustrates the relationship between the F-number F and the size of the permissible circle of confusion.

When the F-number at the boundary between the search state and the examination state is referred to as F', the F-number and the permissible circle of confusion have the relationship illustrated in FIG. 9. When the F-number is smaller than F', the size of the permissible circle of confusion is constant at K·P. When the F-number is larger than F', the size of the permissible circle of confusion is determined by the Airy disk diameter d. Since the Airy disk diameter d increases as the F-number increases (see FIG. 8), the size of the permissible circle of confusion increases in the search state as the F-number increases (see FIG. 9).

Figure 10:
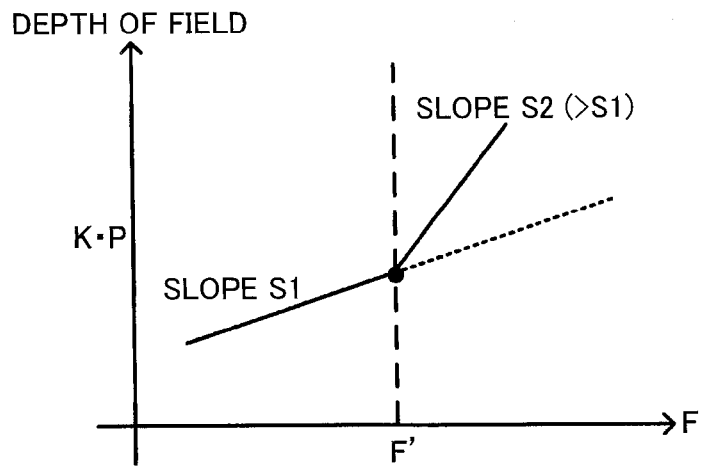
FIG. 10 illustrates the relationship between the depth of field and the F-number F.

The depth of field increases as the F-number increases, and also increases as the size of the permissible circle of confusion increases. Specifically, the depth of field and the F-number have the relationship illustrated in FIG. 10. When the F-number is smaller than F' (examination state), the depth of field increases along a slope S1 as the F-number increases. When the F-number is larger than F' (search state), the depth of field increases along a slope S2 (S2>S1) due to an increase in the F-number and an increase in the size of the permissible circle of confusion.

Figure 11:
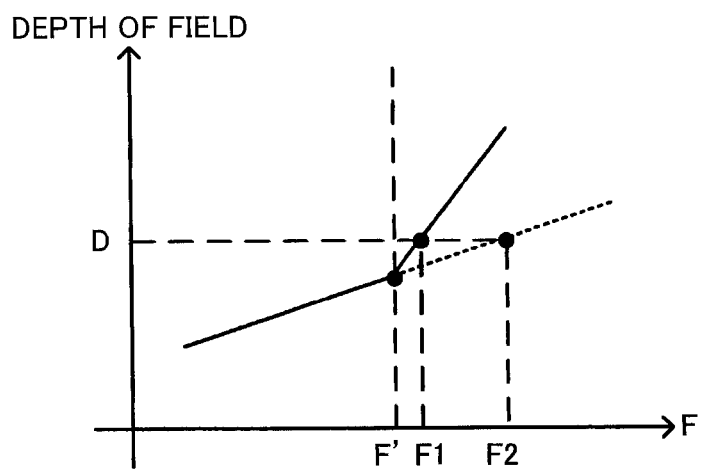
FIG. 11 illustrates the F-number F that implements the depth of field D.

Therefore, the increase rate of the depth of field due to an increase in the F-number can be increased as compared with the case of using the mode (examination state) in which the effects in the diffraction limit are suppressed. This makes it possible to implement the desired depth of field using a small F-number as compared with the case of using the examination state. FIG. 11 illustrates the above advantage. When using the examination state, it is necessary to set the F-number to F2 in order to implement the desired depth of field D. When using the search state, however, the desired depth of field D can be implemented by setting the F-number to F1 (F1<F2).

Specifically, since a small F-number can be used when implementing the depth of field D, a brighter image can be obtained. This is particularly effective for a system that tends to generate a dark image due to a low intensity of light (e.g., narrow-band observation (e.g., NBI) employed for an endoscope system).

2. First Embodiment

Figure 12:
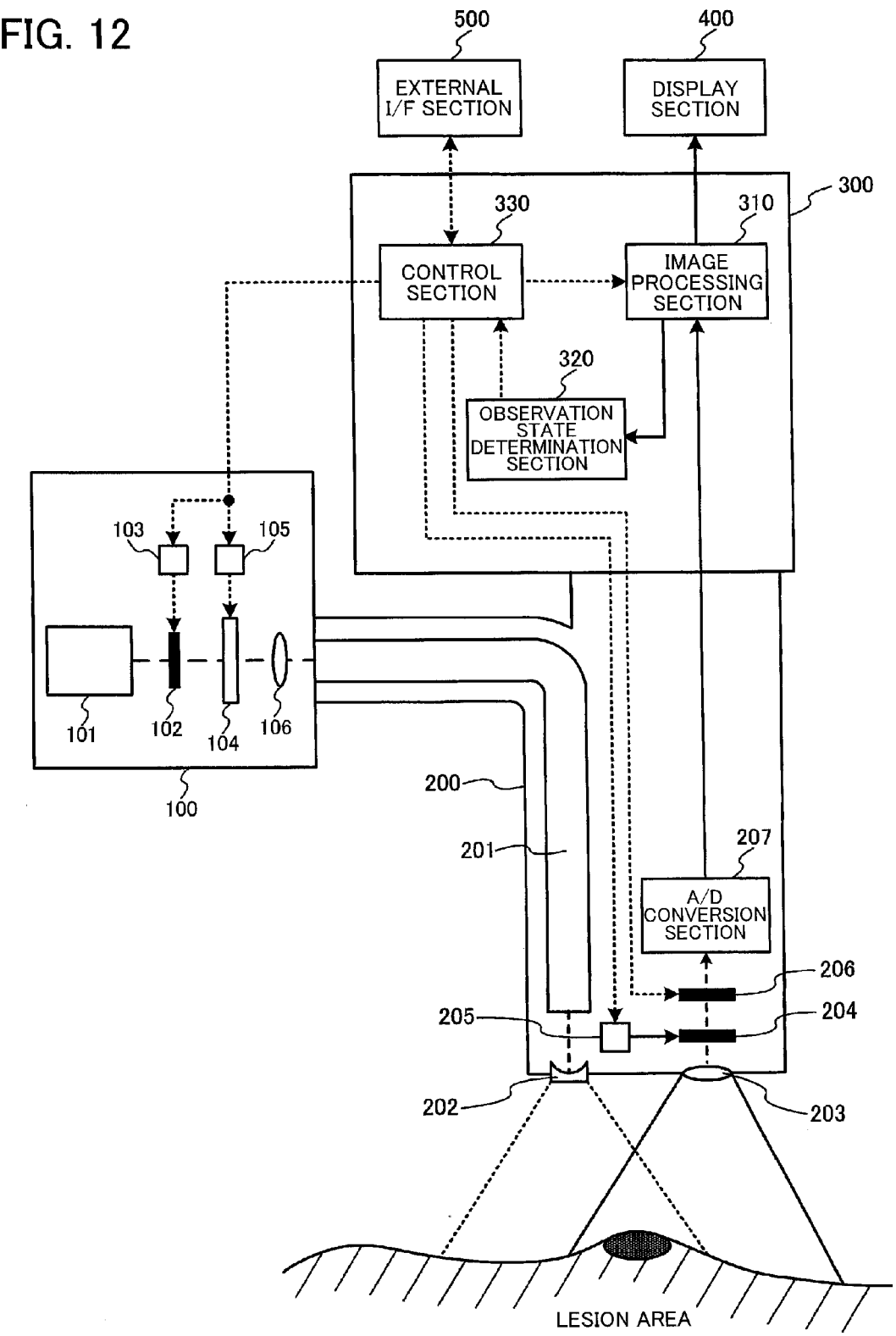
FIG. 12 illustrates a system configuration example according to one embodiment of the invention.

FIG. 12 is a block diagram illustrating the overall configuration of an endoscope system according to a first embodiment of the invention. The endoscope system according to the first embodiment includes a light source section 100, an imaging section 200, a processor section 300, a display section 400, and an external I/F section 500.

The light source section 100 includes a white light source 101, a light source aperture 102, a light source aperture driver section 103 that drives the light source aperture 102, a rotary color filter 104 that has a plurality of spectral transmittances, a rotation driver section 105 that drives the rotary color filter 104, and a condenser lens 106 that focuses light that has spectral characteristics and has passed through the rotary color filter 104 on an incident end face of a light guide fiber 201.

Figure 13:
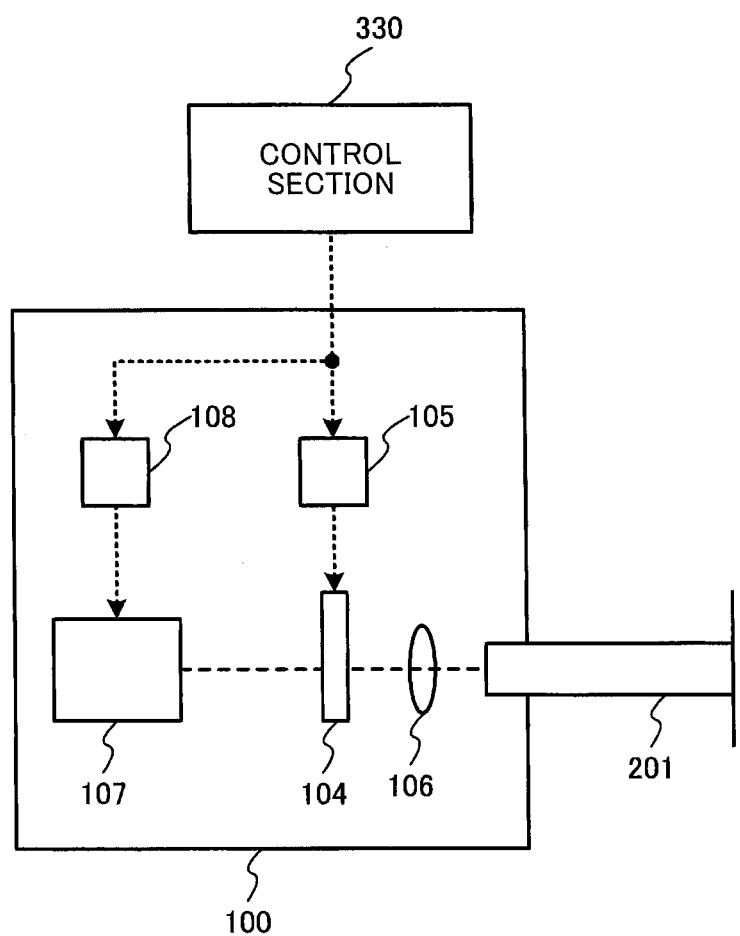
FIG. 13 illustrates a configuration example of a light source section that utilizes an LED light source.

The light source aperture driver section 103 adjusts the intensity of light by opening up or stopping down the light source aperture 102 based on a control signal output from a control section 330 included in the processor section 300. The light source section 100 may include an LED light source 107 and an LED driver section 108 instead of the white light source 101 and the light source aperture 102 (see FIG. 13). The LED driver section 108 adjusts the intensity of light emitted from the LED light source 107 based on a control signal output from the control section 330 included in the processor section 300.

Figure 14:
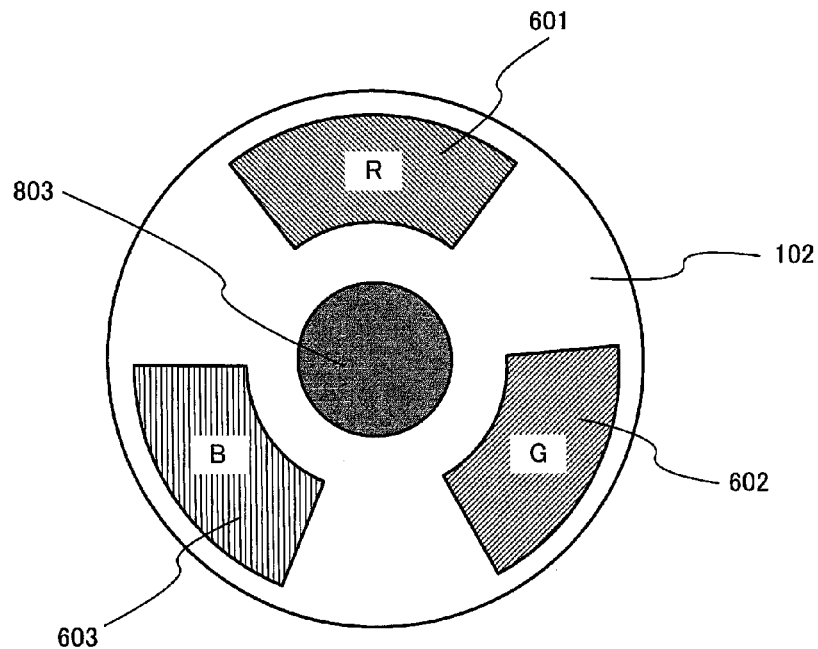
FIG. 14 illustrates a configuration example of a rotary filter.
Figure 15:
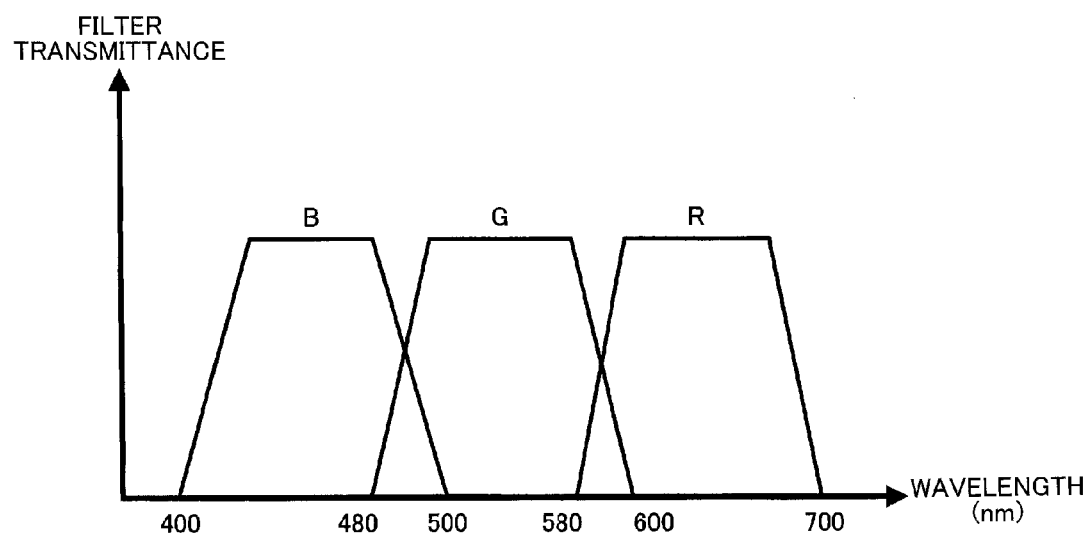
FIG. 15 illustrates the spectral characteristics of a color filter.

As illustrated in FIG. 14, the rotary color filter 104 includes a red color filter 601, a green color filter 602, a blue color filter 603, and a rotary motor 803 (see FIG. 14), for example. The red color filter 601, the green color filter 602, and the blue color filter 603 have the spectral characteristics illustrated in FIG. 15.

The rotation driver section 105 rotates the rotary color filter 104 at a given rotational speed in synchronization with the imaging period of an image sensor 206 based on a control signal output from the control section 330 included in the processor section 300. For example, when rotating the color filter at 20 revolutions per second, each color filter crosses incident white light every 1/60th of a second, and the image sensor 206 completes acquisition and transfer of an image signal of reflected light in each color (R, G, or B) every 1/60th of a second. The image sensor 206 is a monochrome image sensor. Specifically, the endoscope system according to the first embodiment is configured so that an R image signal, a G image signal, and a B image signal are sequentially acquired every 1/60th of a second.

The imaging section 200 is formed to be elongated and flexible (i.e., can be curved) so that the imaging section 200 can be inserted into a body cavity or the like. The imaging section 200 includes the light guide fiber 201 that guides light focused by the light source section 100, an illumination lens 202 that diffuses light that has been guided by the light guide fiber 201, and illuminates an observation target, an objective lens 203 that focuses reflected light that has returned from the observation target, a variable aperture 204, an objective aperture driver section 205 that opens up or stops down the variable aperture 204 under control of the control section 330, the image sensor 206 that detects the focused reflected light, and an A/D conversion section 207 that converts a photoelectrically converted analog signal output from the image sensor 206 into a digital signal. The image sensor 206 is a monochrome single-chip image sensor, and may be implemented by a CCD sensor, a CMOS sensor, or the like.

The processor section 300 includes an image processing section 310, an observation state determination section 320, and the control section 330. The digital image signal converted by the A/D conversion section 207 is transmitted to the image processing section 310. The image signal processed by the image processing section 310 is transmitted to the observation state determination section 320 and the display section 400. The observation state determination section 320 transmits observation state information detected from the image signal to the control section 330. The control section 330 is connected to the light source aperture driver section 103, the rotation driver section 105, the objective aperture driver section 205, the image sensor 206, the image processing section 310, and the external I/F section 500, and controls the light source aperture driver section 103, the rotation driver section 105, the objective aperture driver section 205, the image sensor 206, the image processing section 310, and the external I/F section 500.

The display section 400 is a display (e.g., CRT or liquid crystal monitor) that can display a moving picture (moving image).

The external I/F section 500 is an interface that allows the user to perform an input operation or the like on the imaging device. The external I/F section 500 includes a power switch (power ON/OFF switch), a shutter button (imaging operation start button), a mode (e.g., imaging mode) switch button, and the like. The external I/F section 500 transmits the input information to the control section 330.

The details of the image processing section 310 are described below with reference to FIG. 16. The image processing section 310 includes a preprocessing section 311, a noise reduction section 312, a demosaicing section 313, and a post-processing section 314. The A/D conversion section 207 is connected to the preprocessing section 311. The preprocessing section 311 is connected to the noise reduction section 312. The noise reduction section 312 is connected to the demosaicing section 313. The demosaicing section 313 is connected to the post-processing section 314 and the observation state determination section 320. The post-processing section 314 is connected to the display section 400. The control section 330 is connected to the preprocessing section 311, the noise reduction section 312, the demosaicing section 313, and the post-processing section 314, and controls the preprocessing section 311, the noise reduction section 312, the demosaicing section 313, and the post-processing section 314.

The preprocessing section 311 performs an OB clamp process, a gain control process, and a WB correction process on the digital image signal input from the A/D conversion section 207 using an OB clamp value, a gain correction value, and a WB coefficient stored in the control section 330. The image signal subjected to preprocessing is transmitted to the noise reduction section 312.

The noise reduction section 312 performs a low-pass filter process on the image signal processed by the preprocessing section based on a control signal output from the control section 330. The low-pass filter process further blocks high-frequency noise when a control signal that instructs to enhance the noise reduction process has been transmitted from the control section 330. The image signal subjected to the noise reduction process is transmitted to the demosaicing section 313.

The demosaicing section 313 performs a demosaicing process on the frame-sequential R image signal, G image signal, and B image signal subjected to the noise reduction process by the noise reduction section 312 based on a control signal output from the control section 330. The image signal subjected to the demosaicing process is transmitted to the post-processing section 314 and the observation state determination section 320.

The post-processing section 314 performs a grayscale transformation process, a color process, and a contour enhancement process using a grayscale transformation coefficient, a color conversion coefficient, and a contour enhancement coefficient stored in the control section 330. The image signal subjected to post-processing is transmitted to the display section 400.

Figure 17:
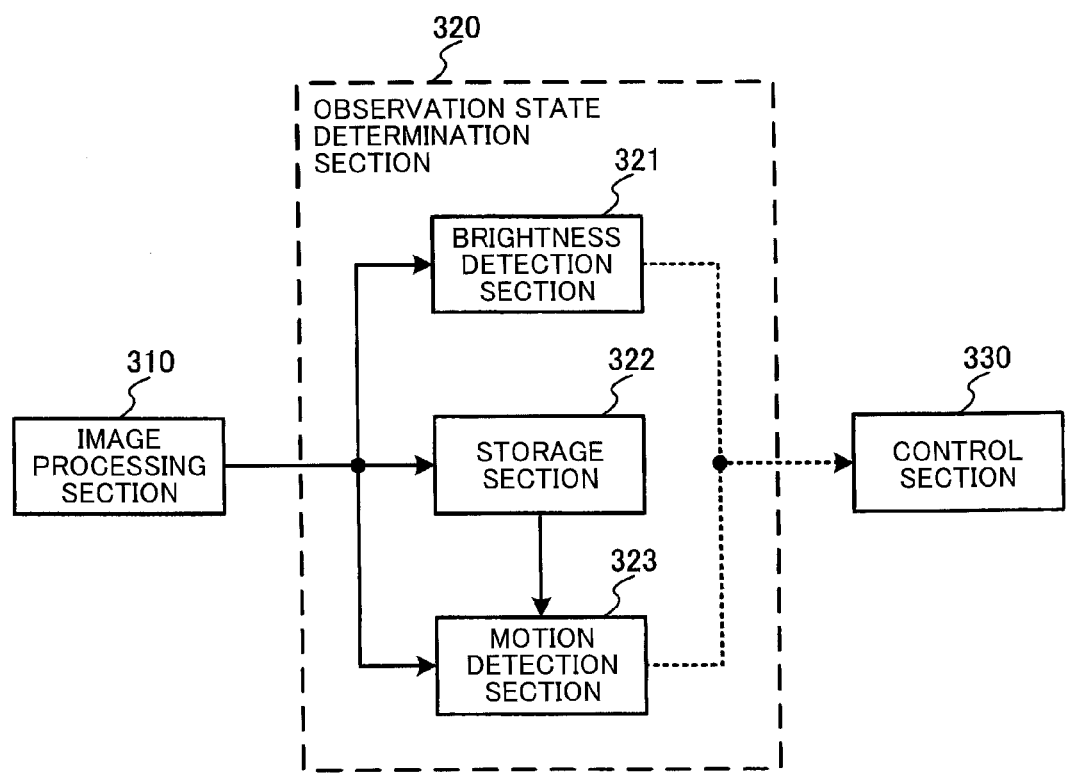
FIG. 17 illustrates a configuration example of an observation state determination section.

The details of the observation state determination section 320 are described below with reference to FIG. 17. The observation state determination section 320 includes a brightness detection section 321, a storage section 322, and a motion detection section 323. The image processing section 310 is connected to the brightness detection section 321, the storage section 322, and the motion detection section 323. The brightness detection section 321 is connected to the control section 330, and transmits brightness information about the image signal. The storage section 322 is connected to the motion detection section 323, and transmits the previous image signal that has been stored at a timing earlier than the image signal input from the image processing section 310 to the motion detection section 323. The motion detection section 323 is connected to the control section 330, and transmits motion information about the image signal.

The brightness detection section 321 detects the brightness information about the image signal input from the image processing section 310. For example, the average luminance value of the entire image is used as the brightness information. Note that the brightness information is not limited to the average luminance value of the entire image, but may be the average luminance value of the center area of the image, or may be the average luminance value of the time-series (consecutive) image signals. The brightness information detected by the brightness detection section 321 is transmitted to the control section 330.

The storage section 322 stores the image signal transmitted from the image processing section 310 (hereinafter may referred to as "current image signal"), and outputs the image signal that has been transmitted from the image processing section 310 at a timing earlier than the current image signal to the motion detection section. More specifically, the current image signal may be the R image signal, the G image signal, or the B image signal. Each color signal is sequentially updated every 1/60th of a second. For example, when the R image signal has been transmitted from the image processing section 310 as the current image signal, the R image signal that has been transmitted from the image processing section 310 immediately prior to the current image signal (hereinafter may referred to as "previous image signal") is transmitted to the motion detection section 323. This also applies to the G image signal and the B image signal.

The motion detection section 323 detects the motion of the object between the current image signal transmitted from the image processing section 310 and the previous image signal stored in the storage section 322. More specifically, the motion detection section 323 compares the current image signal with the previous image signal that corresponds to the same color as the current image signal to calculate the motion of the object. Note that the image signal used for the motion detection process is not limited to the current R image signal, the current G image signal, or the current B image signal. For example, a luminance signal may be calculated from the R image signal, the G image signal, and the B image signal, and the motion detection process may be performed based on the luminance signal.

For example, the current R image signals may be divided into a plurality of blocks, and the motion of the object may be detected based on the previous R image signals on a block basis. This method specifies a position having the smallest difference from an attention block among the blocks into which the current image signals are divided, within the search range of the previous image signals. A vector that indicates the moving direction and the moving amount of the object (hereinafter referred to as "motion vector") corresponding to the attention block is determined by the specified position.

Specifically, the absolute difference value on a block basis or the similarity evaluation value that corresponds to the absolute difference value is calculated for each vector within the search range, and a position having the smallest difference from the attention block is determined based on the calculated absolute difference value or similarity evaluation value to determine the motion vector of the attention block. Each block may include 16×16 pixels, 16×8 pixels, 8×16 pixels, or 8×8 pixels, for example. The absolute value of the motion vector of each block is calculated, and the sum of the absolute value of the motion vector of each block is transmitted to the control section 330 as the motion information.

The details of the control section 330 are described below with reference to FIG. 18. The control section 330 includes an objective aperture control section 331, a light source aperture control section 332, and a selection section 333. The observation state determination section 320 is connected to the objective aperture control section 331 and the light source aperture control section 332. The objective aperture control section 331 is connected to the light source aperture control section 332 and the objective aperture driver section 205. The light source aperture control section 332 is connected to the light source aperture driver section 103 and the selection section 333. The external OF section 500 is connected to the selection section 333. The selection section 333 is connected to the preprocessing section 311, the noise reduction section 312, and the image sensor 206. The control section 330 controls each process performed by the image processing section 310. The control section 330 generates a synchronization signal for acquiring an image from the image sensor 206 in synchronization with the rotation timing of the rotation driver section 105.

Figure 19A:
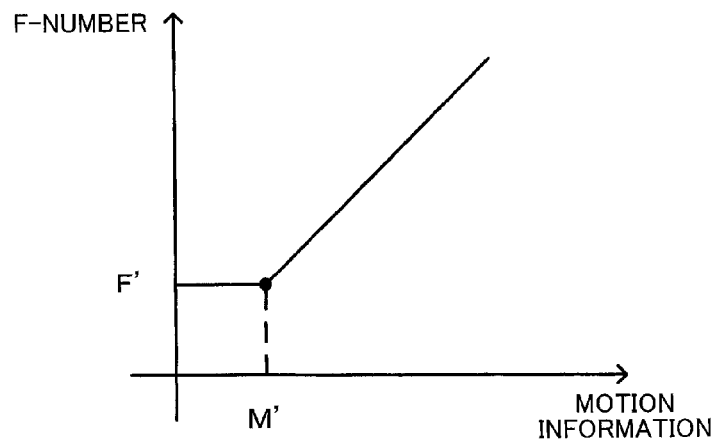
FIGS. 19A to 19C are views illustrating an example of the relationship between motion information and the F-number.
Figure 19B:
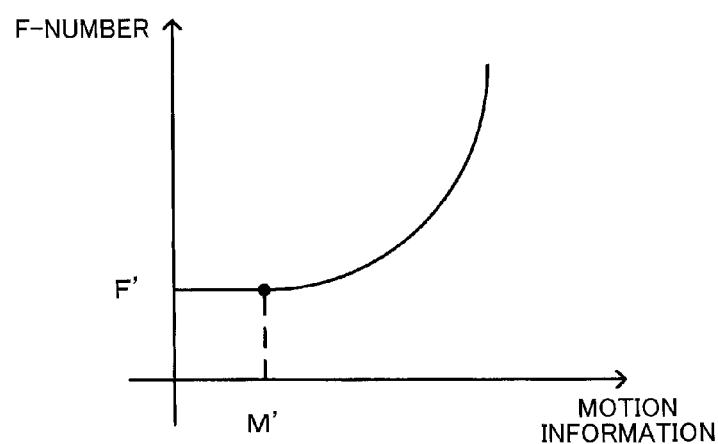
Figure 19C:
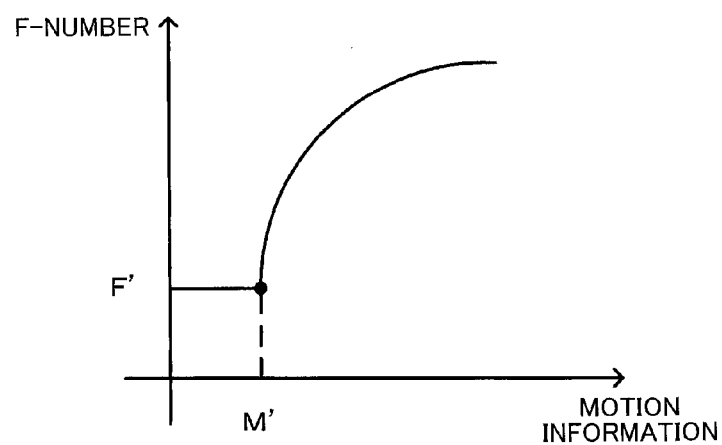

The objective aperture control section 331 transmits a signal that controls the variable objective aperture 204 to the objective aperture driver section 205 based on the motion information detected by the observation state determination section 320. More specifically, the objective aperture control section 331 opens up the aperture (increases the lens opening) when the motion information is smaller than a threshold value M' (see FIG. 19A) so that the permissible circle of confusion is set to a state F' in which the maximum resolution of the image sensor 206 is obtained. This limits the depth of field (i.e., a shallow depth of field is obtained), but makes it possible to obtain a high-resolution image in an in-focus state by fully utilizing the performance of the image sensor. The objective aperture control section 331 stops down the aperture (decreases the lens opening) when the motion information is larger than the threshold value M' so that the permissible circle of confusion has a size that achieves a practical resolution and a practical depth of field. The expression "practical resolution" refers to a resolution that is lower than the maximum resolution of the image sensor 208 and is almost equal to the resolution of an image sensor produced by an old production process, for example. The motion information and the F-number may have the relationship illustrated in FIG. 19B or 19C. The aperture value that has been set corresponding to the motion information is indicated by Fx. The aperture value Fx is transmitted to the light source aperture control section 332 and the objective aperture driver section 205.

The light source aperture control section 332 transmits a signal that controls the light source aperture 102 to the light source aperture driver section 103 based on the brightness information detected by the observation state determination section 320 and an objective aperture control signal. More specifically, when the desired brightness input from the outside in advance is Ya, the detected brightness information is Yb, the objective aperture value set by the objective aperture control section 331 is Fx, the current objective aperture value is Fy, the current light source aperture value is Fz, and the light source aperture value is F1, the light source aperture value F1 can be set using the following expression (9).

$$Fl = Fz \cdot \sqrt{\frac{Yb}{Ya} \cdot \frac{Fy}{Fx}} \quad (9)$$

The light source aperture value F1 that has thus been set is transmitted to the light source aperture driver section 103. When the light source aperture value F1 exceeds the opening limit of the light source aperture 102, a control signal is transmitted to the selection section 333.

The selection section 333 selects a change in frame rate of the image sensor or enhancement of the noise reduction process based on a signal output from the external I/F section 500 only when the control signal has been transmitted from the light source aperture control section 332. More specifically, whether or not to convert the frame rate is set using the external I/F section 500 based on a mode switch request issued by the user using the mode switch button. When the mode has been set to a frame rate conversion mode based on the request from the user, a control signal that decreases the frame rate is transmitted to the image sensor. When the mode is not set to the frame rate conversion mode, a control signal that increases the gain control amount is transmitted to the preprocessing section 311, and a control signal that enhances the noise reduction process is transmitted to the noise reduction section 312.

The exposure time of the captured image per frame increases as a result of decreasing the frame rate, so that a bright image can be obtained. A bright image can also be obtained by increasing the gain control amount. Specifically, the brightness of a dark image can be corrected by a method other than a method that opens up the light source aperture by stopping down the aperture in order to increase the depth of field.

According to the first embodiment, a high-quality image can be obtained in each observation state without requiring the doctor to perform a troublesome operation by automatically detecting a plurality of observation states, so that optimum observation can be implemented corresponding to the objective.

In particular, even when the original resolution of the image sensor cannot be obtained with respect to a small pixel pitch due to the effects of the diffraction limit based on the aperture of the optical system, the object can be observed at the maximum resolution of the image sensor by switching the observation state between a state in which the depth of field is deep and the resolution is low (search state) and a state in which the depth of field is shallow and the resolution is high (examination state).

As a modification, the observation state may be determined by detecting an attention area (e.g., blood vessel structure or lesion area) instead of using the motion detection process. More specifically, whether the observation state is the search state or the examination state may be determined based on whether or not it has been determined that a specific blood vessel structure or a lesion area is present within the captured image. When an attention area has been detected, it is determined that the user (doctor) examines the detected attention area, and the aperture control process or the like that corresponds to the examination state is performed. When an attention area has not been detected, it is determined that the user (doctor) searches an attention area, and the aperture control process or the like that corresponds to the search state is performed. In this case, observation using special light (e.g., narrow band imaging (NBI)) may be performed in order to detect an attention area.

Figure 18:
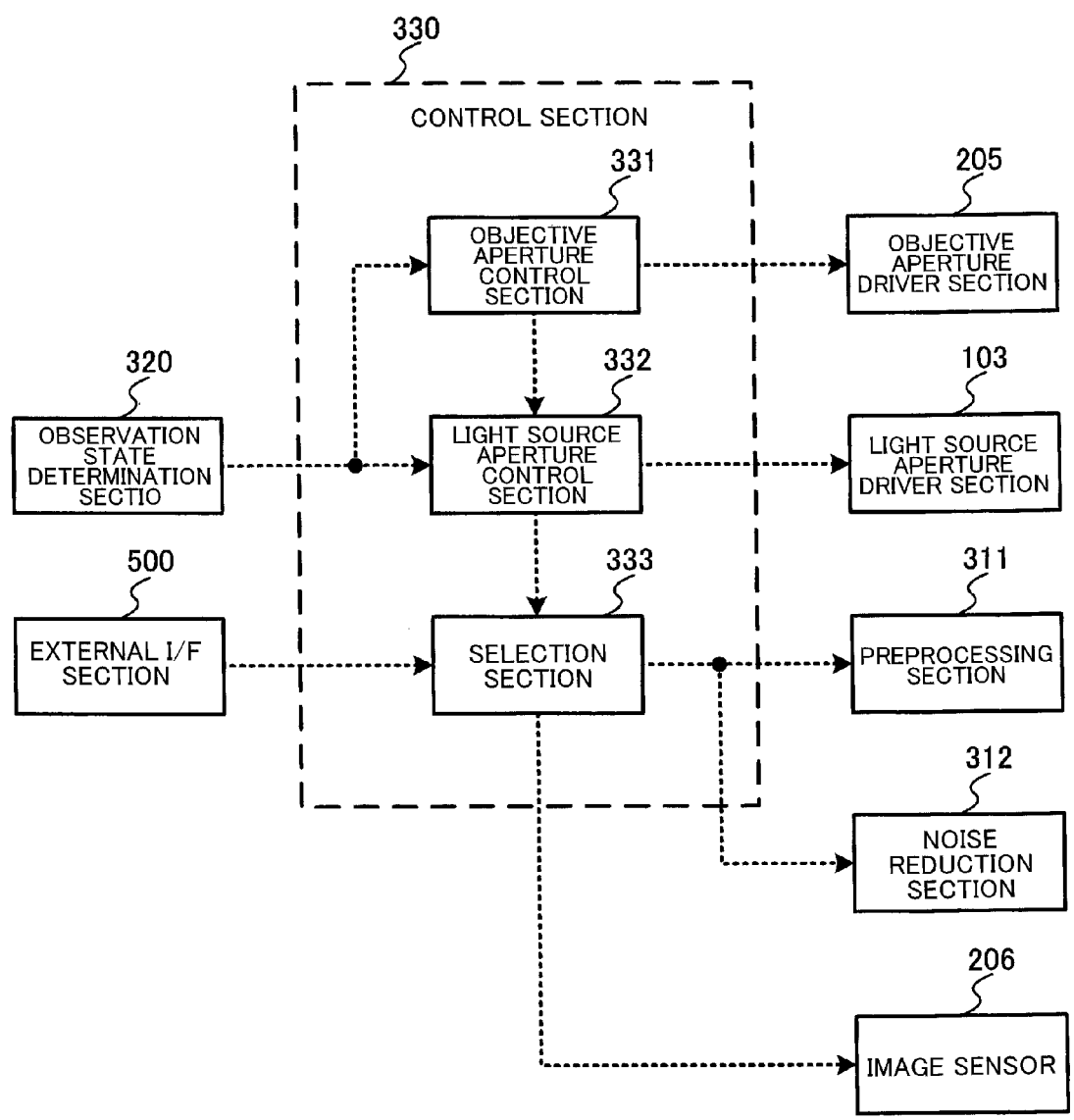
FIG. 18 illustrates a configuration example of a control section.

According to the first embodiment, the endoscope system includes the imaging section 200, the observation state determination section 320 that determines the observation state, and an aperture control section (that corresponds to the objective aperture control section 331 and the light source aperture control section 332 illustrated in FIG. 18, and corresponds to the control section 330 that controls the LED driver section 108 when using an LED light source) that controls an aperture state based on the observation state (see FIG. 12). The imaging section 200 captures the object via the optical system and the image sensor 206. The observation state determination section 320 determines the observation state of the object.

This makes it possible to automatically determine the observation state, and select the aperture state that corresponds to the observation state. Therefore, the user need not perform a troublesome operation (e.g., mode switch operation). In the first observation state (e.g., examination state), an image having a resolution achieved by fully utilizing the performance of the image sensor can be acquired in spite of a shallow depth of field by decreasing the F-number (i.e., suppressing the effects of the diffraction limit). In the second observation state (e.g., search state), a deep depth of field can be implemented in spite of a low resolution by increasing the F-number (i.e., increasing the effects of the diffraction limit by stopping down the aperture as compared with the first observation state).

The observation state determination section 320 may include the motion detection section 323 that detects the motion information that indicates the relative motions of the object and the imaging section 200 (see FIG. 17), and may determine the observation state of the object based on the detection result for the motion information.

This makes it possible to determine the observation state using the motion information. The motion information indicates the relative motions of the object and the imaging section 200. The motion information may indicate a case where the imaging section 200 is stationary and the object makes a motion, a case where the object is stationary and the imaging section 200 makes a motion, or a case where the imaging section 200 and the object make a motion.

The observation state determination section 320 may determine that the observation state of the object is the second observation state when a motion amount indicated by the motion information is larger than a given reference value.

This makes it possible to determine that the observation state is the second observation state when the motion amount is large. The second observation state may be the search state in which the imaging section 200 is moved to a large extent in order to search a lesion area, for example. In this case, since it is desirable to provide an image in which a wide range is in focus, the aperture is stopped down.

The motion detection section 323 may detect the motion information based on an image signal acquired by the imaging section 200 at a first timing, and an image signal acquired by the imaging section 200 at a second timing.

This makes it possible to detect the motion information using image information. Specifically, the motion information is detected based on two different image signals acquired at the first timing and the second timing (i.e., different timings). More specifically, the motion vector between the image signal acquired at the first timing and the image signal acquired at the second timing may be calculated, and used as the motion information. Note that the motion information may be detected using a method other than the method that calculates the motion vector.

The endoscope system may include a light source (e.g., the white light source 101 illustrated in FIG. 12, or the LED light source 107 illustrated in FIG. 13) that illuminates the object, and a light intensity control section (e.g., the control section 330 that controls the light source aperture 102 (see FIG. 18) or the LED driver section 108 (see FIG. 13)) that controls the intensity of light emitted from the light source. The light intensity control section may increase the intensity of light when it has been determined that the observation state is the second observation state as compared with the case where it has been determined that the observation state is the first observation state.

This makes it possible to control the intensity of light. In the second observation state, the aperture is stopped down as compared with the first observation state. Therefore, the entire image darkens, so that the visibility decreases. In order to deal with this problem, the intensity of light emitted from the light source is increased in the second observation state so that the image does not darken.

Figure 16:
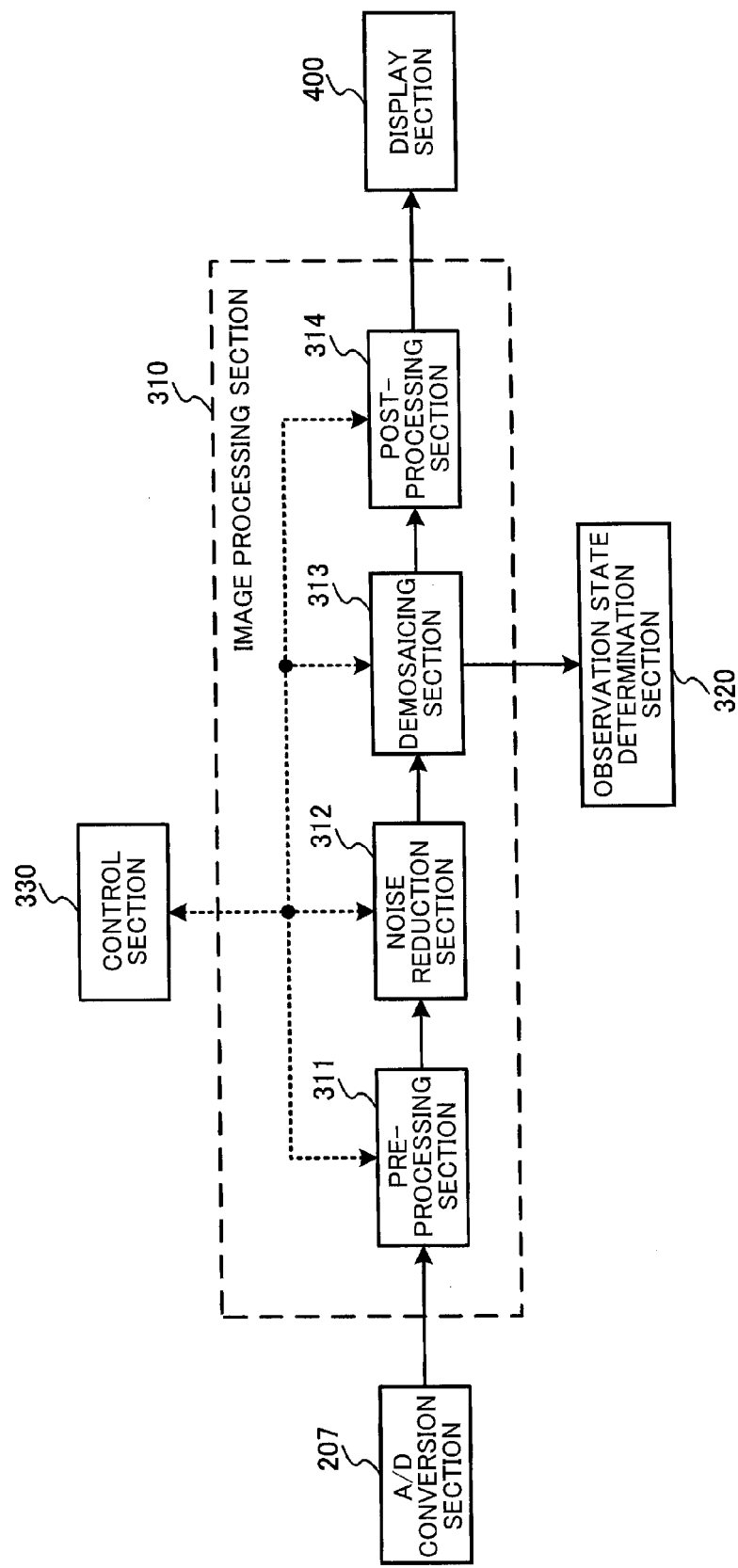
FIG. 16 illustrates a configuration example of an image processing section.

The endoscope system may include the noise reduction section 312 that performs the noise reduction process on the image signal (see FIG. 16). The noise reduction section 312 may perform image processing that enhances the noise reduction process when it has been determined that the observation state is the second observation state as compared with the case where it has been determined that the observation state is the first observation state.

This makes it possible to enhance the noise reduction process in the second observation state. The image darkens in the second observation state since the aperture is stopped down. Therefore, the intensity of light is increased by causing the light source aperture control section 332 to open up the light source aperture 102, for example. When the intensity of light is insufficient even when the intensity of light has been increased, the brightness of the image may be increased by performing a gain-up process. However, since the amount of noise increases due to the gain-up process, it is necessary to perform an appropriate noise reduction process. Therefore, it is desirable to enhance the noise reduction process in the second observation state as compared with the first observation state. In the second observation state (search state), since the resolution has decreased (i.e., high-frequency signal components have been removed) due to the effects of the diffraction limit, it is likely that a high-frequency component is noise, and it is considered that the image quality does not deteriorate to a large extent even if the high-frequency component is reduced.

The endoscope system may include the control section 330 (see FIG. 12), and the control section 330 may control the image sensor 206. The control section 330 may increase the exposure time of the image sensor 206 per frame when it has been determined that the observation state is the second observation state as compared with the case where it has been determined that the observation state is the first observation state.

This makes it possible to control the exposure time of the image sensor 206 per frame. Note that the exposure time refers to the charge storage time of the image sensor (e.g., CCD sensor). Specifically, a bright image signal can be provided even in the second observation state in which the image signal tends to darken, by thus decreasing the frame rate. Note that the movie performance decreases as a result of decreasing the frame rate. Therefore, the user is allowed to determine whether or not to decrease the frame rate.

The observation state determination section 320 may determine the observation state of the object based on the image signal acquired by the imaging section 200.

This makes it possible to determine the observation state based on the image signal. For example, the motion information may be detected based on the image signal (image signals acquired at two different timings), and the observation state may be determined from the detected motion information.

The first embodiment also relates to a control method that includes capturing the object, determining the observation state of the captured Object, controlling the aperture state so that the resolution determined by the diffraction limit due to the aperture of the optical system is equal to or higher than the resolution determined by the image sensor 206 when it has been determined that the observation state is the first observation state (examination state), and stopping down the aperture when it has been determined that the observation state is the second observation state (search state).

This makes it possible to achieve the above effects by applying the method according to the first embodiment to a control method instead of an endoscope system.

The method according to the first embodiment may be applied to an imaging device instead of an endoscope system. In this case, the imaging device includes an imaging section, an observation state determination section that determines the observation state of the object, and an aperture control section that controls the state of an aperture based on the observation state. The aperture control section opens up the aperture to implement the resolution achieved by fully utilizing the performance of the image sensor when it has been determined that the observation state is the first observation state. The aperture control section stops down the aperture when it has been determined that the observation state is the second observation state as compared with the case where it has been determined that the observation state is the first observation state.

This makes it possible to achieve the above effects by applying the method according to the first embodiment to a normal imaging device instead of an endoscope system.

3. Second Embodiment

The configuration according to a second embodiment differs from the configuration according to the first embodiment as to the observation state determination section 320.

The details of the observation state determination section 320 according to the second embodiment are described below with reference to FIG. 20. The observation state determination section 320 includes the brightness detection section 321 and a shape detection section 325. The image processing section 310 is connected to the brightness detection section 321 and the shape detection section 325. The shape detection section 325 is connected to the control section 330, and transmits shape information about the object.

The details of the shape detection section 325 according to the second embodiment are described below. An area 1 and an area 2 (see FIGS. 21A and 21B) are set to the image output from the image processing section 310. An area in which the distance r from the center of the image satisfies "$0 \le r \le r0$" is set to be the area 1, and an area in which the distance r from the center of the image satisfies "$r0 < r$" is set to be the area 2. r0 is input from the outside in advance as a constant that distinguishes the center area and the peripheral area of the image. The average luminance L1 of the area 1 and the average luminance L2 of the area 2 are calculated. The relationship between the average luminance L1 and the average luminance L2 of each shape of the object is described below with reference to FIGS. 21A to 22B. A bold line in FIGS. 22A and 22B indicates the shape of tissue (object), and a broken line indicates the angle of view of the imaging section 200. A range that almost coincides with the angle of view is illuminated by an illumination section (not illustrated) that is provided near the imaging section.

As illustrated in FIG. 22A, when the imaging section 200 moves through a hollow tubular object (search state), the object positioned around the center of the image is distant from the imaging section 200 as compared with the object positioned in the peripheral area of the image. Therefore, the area 2 that is the peripheral area of the image is brighter than the area 1 that is the center area of the image (see FIG. 22A). When the imaging section 200 faces the wall of the object (examination state), the imaging section 200 is adjusted so that the attention area is positioned around the center of the image (see FIG. 22B). In this case, since the distance between the imaging section and the object differs to only a small extent between the center area and the peripheral area of the image, an image in which the center area is brighter than the peripheral area is normally obtained due to the intensity distribution of illumination light, mechanical vignetting of the optical system, and the like (see FIG. 22B). The shape information L is calculated by the following expression (10).

$$L = L2/L1 \tag{10}$$

The shape information L is transmitted to the control section 330. Although the second embodiment utilizes the luminance of the image signal as the feature quantity, a feature quantity other than the luminance may also be used. For example, a known frequency resolution process may be performed on the input image signal, and the shape information may be detected from the frequency characteristics.

The control section 330 performs the above process using the shape information instead of the motion information used in the first embodiment.

According to the second embodiment, a high-quality image can be obtained when the doctor closely observes the attention area, and a deep image can be obtained when the imaging section moves through a tubular object by automatically detecting the shape of the object, so that optimum observation can be implemented corresponding to the objective.

The above process utilizes the shape information in order to determine whether or not the imaging section faces the object (see FIGS. 22A and 22B). Specifically, it suffices that the endoscope system include a facing state detection section 326 (see FIG. 23) that determines whether or not the imaging section faces the object (i.e., the shape information need not necessarily be acquired). For example, a distance measurement section (e.g., infrared active sensor) that measures the distance from the object may be provided to the imaging section 200, and a distance information acquisition section 327 may acquire distance information about the distance from the object. The distance indicated by the distance information is long when the imaging section does not face the object (see FIG. 22A), and is short when the imaging section faces the object (see FIG. 22B). For example, a given threshold value may be provided for the distance from the object, and the distance from the object may be compared with the threshold value.

Figure 20:
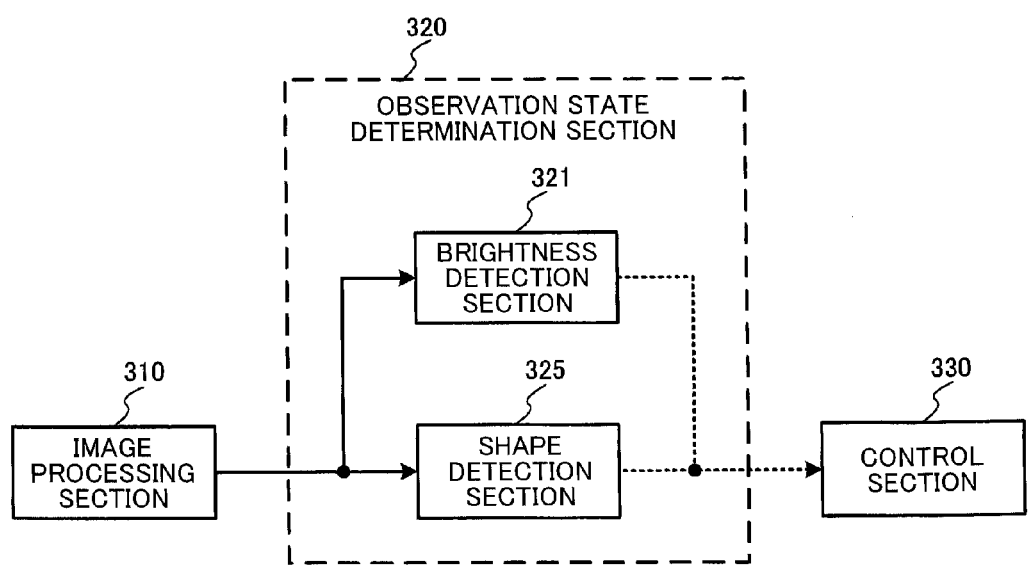
FIG. 20 illustrates another configuration example of an observation state determination section.

According to the second embodiment, the observation state determination section 320 includes the shape detection section 325 that detects the shape information that indicates the shape of the object viewed from the imaging section 200 (see FIG. 20). The observation state determination section 320 determines the observation state of the object based on the shape information. For example, the observation state determination section 320 may determine that the observation state is the first observation state when it is estimated that the shape indicated by the shape information is a planar shape.

This makes it possible to determine the observation state based on the shape information about the object. The shape information may be information that indicates the shape of an attention area viewed from the imaging section 200 (see FIGS. 22A and 22B), for example. In FIG. 22A, the attention area is part of the hollow tubular shape. In FIG. 22B, the attention area has a planar shape. since it is considered that the state illustrated in FIG. 22B is the examination state in which the doctor closely observes the attention area, it is determined that the observation state is the first observation state when it is estimated that the shape indicated by the shape information is a planar shape.

The observation state determination section 320 may estimate whether or not the shape indicated by the shape information is a planar shape based on the feature quantity in the center area and the feature quantity in the peripheral area indicated by the image signal.

This makes it possible to estimate the shape indicated by the shape information using the feature quantity indicated by the image information. For example, the shape indicated by the shape information may be estimated from the ratio of the luminance information (brightness information) in the center area to the luminance information in the peripheral area (see FIGS. 21A and 21B). When the doctor observes the hollow tubular object illustrated in FIG. 22A, the center area of the image is dark, and the peripheral area of the image is bright (see FIG. 21A). When the doctor observes the planar object illustrated in FIG. 22B, the center area of the image is bright, and the peripheral area of the image is dark (see FIG. 21B). Therefore, the shape can be estimated using the expression (10).

Figure 23:
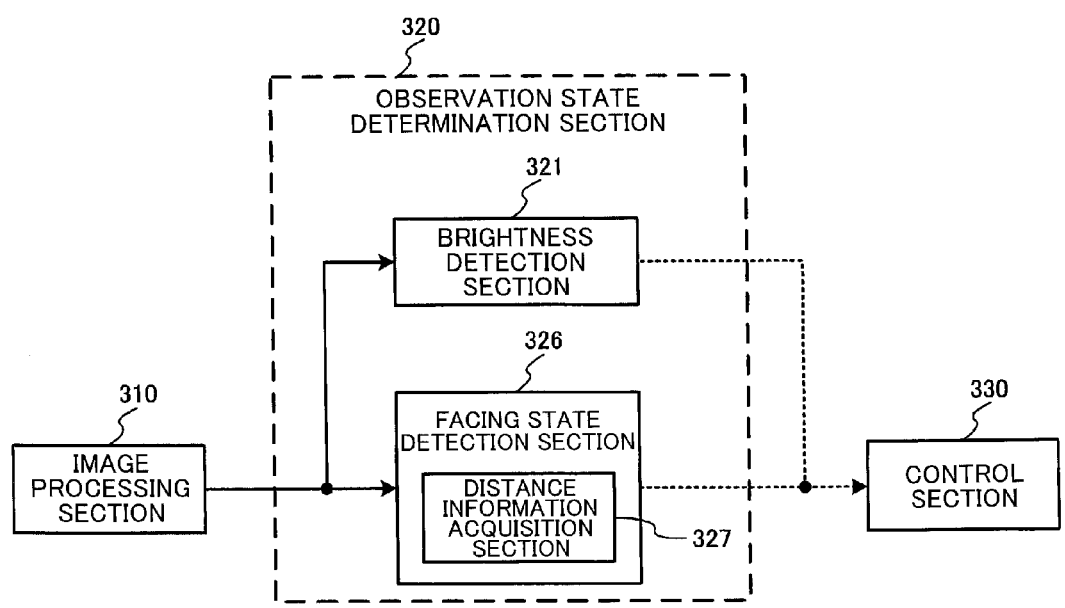
FIG. 23 illustrates still another configuration example of an observation state determination section.

The observation state determination section 320 may include the facing state detection section 326 that detects whether or not the imaging section 200 faces the object (see FIG. 23). The observation state determination section 320 may determine the observation state of the object based on the detection result of the facing state detection section 326. The observation state determination section 320 may determine that the observation state of the object is the first observation state when it has been detected that the imaging section 200 faces the object.

This makes it possible to determine the observation state without determining the shape of the object by determining whether or not the imaging section 200 faces the object. For example, it suffices to detect the difference between the image illustrated in FIG. 22A and the image illustrated in FIG. 22B. It is considered that the user closely observes (examines) the object when it has been detected that the imaging section 200 faces the object (see FIG. 22B), and it is determined that the observation state is the first observation state.

The facing state detection section 326 may include the distance information acquisition section 327 that acquires the distance information that indicates the distance between the imaging section 200 and the object (see FIG. 23). The facing state detection section 326 may determine that the imaging section 200 faces the object when the distance indicated by the distance information is smaller than a given threshold value.

This makes it possible to determine whether or not the imaging section 200 faces the object using the distance information. Specifically, the distance indicated by the distance information is long when the imaging section 200 does not face the object (see FIG. 22A), and is short when the imaging section 200 faces the object (see FIG. 22B). Therefore, it is possible to determine whether or not the imaging section 200 faces the object using the distance information by setting an appropriate threshold value, and making determination using the threshold value.

The first and second embodiments according to the invention and the modifications thereof have been described above. Note that the invention is not limited thereto. Various modifications and variations may be made of the first and second embodiments and the modifications thereof without departing from the scope of the invention. A plurality of elements described in connection with the first and second embodiments and the modifications thereof may be appropriately combined to implement various configurations. For example, an arbitrary element may be omitted from the elements described in connection with the first and second embodiments and the modifications thereof. Some of the elements described in connection with different embodiments or modifications thereof may be appropriately combined. Specifically, various modifications and applications are possible without materially departing from the novel teachings and advantages of the invention.

What is claimed is:

1. An endoscope system comprising:
an imaging section comprising:
an optical system comprising an aperture; and
an image sensor configured to acquire an image signal of an object based on light passing through the aperture; and
a processor comprising hardware, the processor being configured to implement:
an observation state determination section configured to determine an observation state of the imaging section; and
an aperture control section configured to:
control a state of the aperture so that a resolution determined by a diffraction limit due to the aperture is equal to or higher than a resolution determined by the image sensor, based on a determination by the observation state determination section that the observation state is an examination state, and
stop down the aperture as compared with the state of the aperture in the examination state, based on a determination by the observation state determination section that the observation state is a search state.

2. The endoscope system as defined in claim 1,
wherein the observation state determination section comprises a motion detection section configured to detect motion information that indicates relative motions of the object and the imaging section, and
wherein the observation state determination section is configured to determine the observation state based on the motion information detected by the motion detection section.

3. The endoscope system as defined in claim 2, wherein the observation state determination section is configured to determine that the observation state is the search state based on the motion information indicating that a motion amount is larger than a given reference value.

4. The endoscope system as defined in claim 2, wherein the motion detection section is configured to detect the motion information based on an image signal acquired by the imaging sensor at a first timing, and an image signal acquired by the imaging sensor at a second timing.

5. The endoscope system as defined in claim 1,
further comprising a light source configured to emit illumination light to the object,
wherein the processor is further configured to implement a light intensity control section configured to control an intensity of the illumination light emitted from the light source, and
wherein the light intensity control section is configured to increase the intensity of the illumination light emitted from the light source based on the determination by the observation state determination section that the observation state is the search state as compared with a case where the observation state determination section has determined that the observation state is the examination state.

6. The endoscope system as defined in claim 1,
wherein the processor is further configured to implement a noise reduction section configured to perform a noise reduction process on the image signal acquired by the imaging sensor, and
wherein the noise reduction section is configured to perform image processing that enhances the noise reduction process based on the determination by the observation state determination section that the observation state is the search state as compared with a case where the observation state determination section has determined that the observation state is the examination state.

7. The endoscope system as defined in claim 1,
wherein the processor is further configured to implement a control section configured to control the image sensor, and
wherein the control section is configured to increase an exposure time per frame of the image sensor based on the determination by the observation state determination section that the observation state is the search state as compared with a case where the observation state determination section has determined that the observation state is the examination state.

8. The endoscope system as defined in claim 1,
wherein the observation state determination section comprises a shape detection section configured to detect shape information of the object viewed from the imaging section, and
wherein the observation state determination section is configured to determine the observation state based on the shape information.

9. The endoscope system as defined in claim 8, wherein the observation state determination section is configured to:
estimate a shape indicated by the shape information detected by the shape detection section; and
determine that the observation state is the examination state based on an estimation that the shape is a planar shape.

10. The endoscope system as defined in claim 9, wherein the observation state determination section is configured to estimate whether or not the shape is the planar shape based on:
a feature quantity in a center area of an image indicated by an image signal acquired by the imaging sensor; and
a feature quantity in a peripheral area of image indicated by the image signal.

11. The endoscope system as defined in claim 1,
wherein the observation state determination section comprises a facing state detection section configured to detect whether or not the imaging section faces the object, and
wherein the observation state determination section is configured to determine the observation state based on a detection result of the facing state detection section.

12. The endoscope system as defined in claim 11, wherein the observation state determination section is configured to determine that the observation state is the examination state based on a detection by the facing state detection section that the imaging section faces the object when acquiring the image signal of the object.

13. The endoscope system as defined in claim 11,
wherein the facing state detection section comprises a distance information acquisition section that acquires distance information that indicates a distance between the imaging section and the object, and
wherein the facing state detection section is configured to determine that the imaging section faces the object based on distance information that indicates that the distance between the image section and the object is smaller than a given threshold value.

14. The endoscope system as defined in claim 1, wherein the observation state determination section is configured to determine the observation state based on the image signal acquired by the imaging sensor.

15. The endoscope system as defined in claim 1,
wherein the observation state determination section is configured to detect information indicating one of:
priority given to the resolution; and
priority given to the depth of field of the imaging section,
wherein the observation state determination section is configured to determine the observation state based on the detected information.

16. The endoscope system as defined in claim 15, wherein the information comprises one or more of:
motion information that indicates relative motions of the object and the imaging section;
shape information of the object viewed from the imaging section; and
facing state information indicating whether or not the imaging section faces the object.

17. A method comprising:
acquiring an image signal of an object via an imaging section comprising:
an optical system comprising an aperture; and
an image sensor;
determining, by a processor comprising hardware, an observation state of the imaging section;
controlling, by the processor, a state of the aperture so that a resolution determined by a diffraction limit due to the aperture is equal to or higher than a resolution determined by the image sensor, based on a determination that the observation state is an examination state; and
stopping down, by the processor, the aperture as compared with the state of the aperture in the examination state based on a determination that the observation state is a search state.

18. An imaging device comprising:
an imaging section comprising:
an optical system comprising an aperture; and
an image sensor configured to acquire an image signal of an object based on light passing through the aperture; and
a processor comprising hardware, the processor being configured to implement:
an observation state determination section configured to determine an observation state of the imaging section; and
an aperture control section configured to:
control a state of the aperture so that a resolution determined by a diffraction limit due to the aperture is equal to or higher than a resolution determined by the image sensor, based on a determination by the observation state determination section that the observation state is an examination state, and
stop down the aperture as compared with the state of the aperture in the examination state, based on a determination by the observation state determination section that the observation state is a search state.

* * * * *